(12) United States Patent
Druzgala et al.

(10) Patent No.: US 6,608,097 B2
(45) Date of Patent: Aug. 19, 2003

(54) MATERIALS AND METHODS FOR THE TREATMENT OF HYPERTENSION AND ANGINA

(75) Inventors: Pascal Druzgala, Santa Rosa, CA (US); Peter G. Milner, Los Altos Hills, CA (US); Jürg Pfister, Los Altos, CA (US); Xiaoming Zhang, Campbell, CA (US)

(73) Assignee: ARYx Therapeutics, Santa Clara, CA (US)

( * ) Notice: Subject to any disclaimer, the term of this patent is extended or adjusted under 35 U.S.C. 154(b) by 0 days.

(21) Appl. No.: 10/269,139

(22) Filed: Oct. 10, 2002

(65) Prior Publication Data

US 2003/0130330 A1 Jul. 10, 2003

Related U.S. Application Data

(60) Provisional application No. 60/328,588, filed on Oct. 10, 2001.

(51) Int. Cl.[7] .................. A61K 31/4184; C07D 235/14; C07D 235/16
(52) U.S. Cl. ..................... 514/394; 548/309.7
(58) Field of Search ........................ 548/309.7; 514/394

(56) References Cited

U.S. PATENT DOCUMENTS

| | | | |
|---|---|---|---|
| 4,808,605 A | 2/1989 | Branca et al. | |
| 5,620,975 A | 4/1997 | Clozel et al. | |

FOREIGN PATENT DOCUMENTS

| | | | |
|---|---|---|---|
| EP | 0 524 512 A2 | 1/1993 | |
| JP | 11 035483 A | 2/1999 | |

OTHER PUBLICATIONS

Rutledge et al., European Journal of Pharmacology, 280 (1995), pp. 155–158.*

Bursztyn, M., et al., "Mibefradil, a novel calcium antagonist, in elderly patients with hypertension: Favorable hemodynamics and pharmacokinetics", *American Heart Journal*, Aug. 1997, pp. 238–247, vol. 134, No. 2, Pt. 1, Mosby–Year Book, Inc.

De Ponti, F., et al., "QT–interval prolongation by non–cardiac drugs: lessons to be learned from recent experience", *Eur J Clin Pharmacol*, 2000, pp. 1–18, vol. 56, Springer–Verlag.

Dershwitz, M., et al., "Pharmacokinetics and Pharmacodynamics of Remifentanil in Volunteer Subjects with Severe Liver Disease", *Anesthesiology*, Apr. 1996, pp. 812–820, vol. 84, No. 4, American Society of Anesthesiologists, Inc., Lippincott–Raven Publishers.

Kostrubsky, V., et al., "The Role of Conjugation in Hepatotoxicity of Troglitazone in Human and Porcine Hepatocyte Cultures", *Drug Metabolism and Disposition*, 2000, pp. 1192–1197, vol. 28, No. 10, The American Society for Pharmacology and Experimental Therapeutics.

Selnick, H., et al., "Class–III Antiarrhythmic Activity in Vivo By Selective Blockade of the Slowly Activating Cardiac Delayed Rectifier Potassium Current $I_{Ks}$ by (R)–2–(2,4–Triflouromethyl)–N[2–oxo–5–phenyl–1–(2,2,2–trifluoroethyl)–2,3–dihydro–1H–benzo[e][1,4] diazepin–3–yl] acetamide," *J. Med. Chem.*, Nov. 1997, pp. 3865–3868, vol. 40, No. 24, American Chemical Society.

Vandenberg, J., et al., "HERG K+ channels: friend and foe", *Trends in Pharmacological Sciences*, May 2001, pp. 240–246, vol. 22, No. 5, Elsevier Science, Ltd.

* cited by examiner

*Primary Examiner*—Laura L. Stockton
(74) *Attorney, Agent, or Firm*—Saliwanchik, Lloyd & Saliwanchik

(57) ABSTRACT

The subject invention provides useful and novel calcium channel blockers based upon mibefradil. The subject invention also provides methods for synthesizing the compounds of the invention. The invention also provides methods for the control or prevention of hypertension, angina pectoris, ischemia, arrhythmias, and cardiac insufficiency in a patient by administering a compound, or composition, of the invention to an individual in need of such treatment.

14 Claims, 12 Drawing Sheets

Verapamil            Diltiazem

Nifedipine           Mibefradil

Mibefradil primary inactive metabolite
X = bond, CH$_2$, or OCH$_2$

Hydrolytic enzymes soft analog
R = lower alkyl optionally
   substituted by OH or NH$_2$,
X is as defined above primary inactive metabolite Hydrolytic enzymes soft analog
R = lower alkyl optionally
substituted by OH or NH$_2$ primary inactive metabolite
n = 1 to 3

Hydrolytic enzymes soft analog
n = 1 to 3
R = lower alkyl optionally substituted by OH or NH$_2$ primary inactive metabolite
n = 1 to 3

Hydrolytic enzymes soft analog
n = 1 to 3
R = lower alkyl optionally
    substituted by OH or $NH_2$ primary inactive metabolite Hydrolytic enzymes soft analog
R = lower alkyl optionally
   substituted by OH or NH$_2$ primary inactive metabolite
n = 1 to 3

Hydrolytic enzymes soft analog
n = 1 to 3
X = O, NH, NR where R
   is lower alkyl
Y = optionally substituted aryl
   or heterocyclyl primary inactive metabolite
n = 0 to 2
X = O, S, SO, SO$_2$, NH, NR or N(CH$_2$)$_m$COOH
  where m is 0 or 2
Y = aryl or heterocyclyl substituted with (CH$_2$)$_m$COOH
  where m is 0 to 2

Hydrolytic enzymes soft analog
n = 0 to 2
X = O, S, SO, SO$_2$, NH, NR or N(CH$_2$)$_m$COOR
  where m is 0 or 2
Y = aryl or heterocyclyl substituted with (CH$_2$)$_m$COOR
  where m is 0 to 2
R = lower alkyl optionally substituted by OH or NH$_2$ a, iPrCOCH$_2$COOEt, NaOEt; b, conc. H$_2$SO$_4$; c, ROH, H$^+$; d, H$_2$, Pd/C; e, LDA; f, BrCH$_2$CH$_2$OTHP; g, H$^+$; h, TsCl, TEA; i, 2-(N-methylaminopropyl)benzimidazole, K$_2$CO$_3$ a, H₂, Pd/C; b, Br(CH₂)$_n$COOR, K₂CO₃, DMF; c, MeOCH₂COCl, TEA, DMAP a, BuLi, THF; b, Br(CH₂)$_n$COOR a, N-methylbenzylamine, K₂CO₃; b, H₂, Pd/C; c, Br(CH₂)ₙCO-X-Y, K₂CO₃; d, MeOCH₂COCl, TEA, DMAP a, BrCH₂CH₂(CH₂)ₙCO-X-Y, NaI, K₂CO₃, DMF

MATERIALS AND METHODS FOR THE TREATMENT OF HYPERTENSION AND ANGINA

CROSS-REFERENCE TO RELATED APPLICATION

This application claims the benefit of U.S. Provisional Application Ser. No. 60/328,588, filed Oct. 10, 2001.

BACKGROUND OF THE INVENTION

Adverse drug-drug interactions (DDI), elevation of liver function test (LFT) values, and QT prolongation leading to torsades de pointes (TDP) are three major reasons why drug candidates fail to obtain FDA approval. All these causes are, to some extent metabolism-based.

Oxidative metabolism is the primary metabolic pathway by which most drugs (xenobiotics) are eliminated. It is also the major source of drug toxicity, either intrinsic toxicity or toxicity due to drug-drug interactions (DDI). Adverse DDI as well as intrinsic toxicity due to metabolites are a major reason for the failure of drug candidates in late-stage clinical trials. Many DDI are metabolism based, i.e., two or more drugs compete for the same metabolizing enzyme in the cytochrome P450 system (CYP450) [Guengerich, F. P. (1997) Role of cytochrome P450 enzymes in drug-drug interactions. In: Drug-drug interactions: scientific and regulatory perspectives. Li, A P (ed.)Academic Press, San Diego pp7–35 and Shen, W. W. (1995) Int. J. Psychiatry Med. 25:277–290]. Non-oxidative metabolic systems, such as hydrolytic enzymes, on the other hand, do not depend on co-factors; are not inducible; have a high substrate capacity; do not have a high degree of inter-individual variations in man; and are present in most tissues and organs. Non-oxidative metabolic systems are, therefore, much more reliable.

Metabolism-based DDI take place when two (2) or more drugs compete for metabolism by the same enzyme. These metabolic interactions become relevant to DDI when the metabolic system is inducible or/and easily saturable. Such metabolic interactions lead to modification of the pharmacokinetics of the drugs and potential toxicity.

Multiple-drug therapy is a common practice, particularly in patients with several diseases or conditions. Whenever two or more drugs are administered over similar or overlapping time periods, the possibility of drug interactions exists. The ability of a single CYP to metabolize multiple substrates is responsible for the large number of documented clinically significant drug interactions associated with CYP inhibition [Shen, W. W. (1995) Int. J. Psychiatry Med. 25:277–290; Riesenman, C. (1995) Pharmacotherapy 15:84S–99S; and Somogyi, A. et al. (1987) Clin. Pharmacokinet. 12:321–366]. The inhibition of drug metabolism by competition for the same enzyme may result in undesirable elevation in plasma drug concentration. In addition, drug interactions can also occur as a result of induction of several cytochrome P enzymes (CYPs) following prolonged drug treatment.

Enzymes of the CYP450 system are ubiquitous oxidative enzymes found in prokaryotes and eukaryotes. They exist as a superfamily of closely related isozymes, whose substrates comprise a wide variety of structurally unrelated compounds. The enzymes can exhibit broad substrate specificity, but a particular substrate may also be metabolized by several different isozymes. CYP450 play a primary role in the metabolism of drugs and xenobiotics.

The clinical significance of a metabolic drug-drug interaction depends on the magnitude of the change in the concentration of active species (parent drug and/or active metabolites) at the site of pharmacological action and the therapeutic index of the drug. Observed changes arising from metabolic drug-drug interactions can be substantial (e.g., an order of magnitude or more decrease or increase in the blood and tissue concentrations of a drug or metabolite) and can include formation of toxic metabolites or increased exposure to a toxic parent compound.

Examples of substantially changed exposure associated with administration of another drug include (1) increased levels of terfenadine, cisapride, or astemizole with ketoconazole or erythromycin (inhibition of CYP3A4); (2) increased levels of simvastatin and its acid metabolite with mibefradil or itraconazole (inhibition of CYP3A4); (3) increased levels of desipramine with fluoxetine, paroxetine, or quinidine (inhibition of CYP2D6); and (4) decreased carbamazepine levels with rifampin (induction of CYP3A4).

These large changes in exposure can alter the safety and efficacy profile of a drug and/or its active metabolites in important ways. This is most obvious and expected for a drug with a narrow therapeutic range (NTR), but is also possible for non-NTR drugs as well (e.g., HMG CoA reductase inhibitors). Patients receiving anticoagulants, antidepressants or cardiovascular drugs are at a much greater risk than other patients because of the narrow therapeutic index of these drugs. Although most metabolic drug-drug interactions that can occur with these agents are manageable, usually by appropriate dosage adjustment, a number of these DDI are potentially life threatening.

As an example, mibefradil (Posicor®), a calcium channel blocker has been used for the management of hypertension and chronic stable angina [Bursztyn, M., et al. (1997). Am. Heart J. 134:238–247]. Mibefradil inhibits CYP3A4 and interferes with the metabolism of CYP3A4 substrates. Several clinical trials described the overall safety of mibefradil. However, the populations studied were probably healthier and more closely supervised than what is seen in routine clinical practice. After potentially serious interactions between mibefradil and beta-blockers, digoxin, verapamil, and diltiazem, were reported, mibefradil was voluntarily withdrawn from the market in 1998.

Clinicians began the switch from mibefradil to alternative antihypertensive agents, often choosing dihydropyridine-type calcium-channel blockers (CCB), such as nifedipine. A report described four cases of cardiogenic shock in patients taking mibefradil and beta-blockers who were switched to dihydropridine CCBs after withdrawal of mibefradil from the market. One case resulted in death; the other 3 patients survived episodes of cardiogenic shock requiring intensive support of heart rate and blood pressure. All cases occurred within 24 hours of discontinuing mibefradil and initiating the dihydropyridine CCBs. This serious drug-drug interaction probably occurred for two reasons. First, both mibefradil and dihydropyridines are substrates for CYP3A4, making this a potential mechanism. Second, mibefradil has a long half-life (up to 24 hours), with therapeutic levels of the agent likely to have been present within 24 hours of discontinuation.

The non-oxidative metabolic concept of this invention is also illustrated by fluvoxamine (Luvox®). Fluvoxamine is a serotonin reuptake inhibitor that is useful in the treatment of certain compulsive disorders in man. Fluvoxamine was developed at a time when in vitro predictive models of metabolic DDI were not an integral part of the lead optimization process. Because of that, its metabolic DDI liabilities were discovered, after the drug had been approved.

Fluvoxamine is metabolized in a stepwise manner by CYP450 system to give 3 metabolites having progressively higher oxidative levels: an O-desmethyl (an alcohol), an aldehyde, and finally a carboxylic acid metabolite which is the major metabolite in man. The major metabolite does not undergo any further metabolism and is safely eliminated by renal filtration. This sequence of oxidative events is responsible for DDI and toxicity in man.

An alternate, non-CYP450 metabolic pathway, designed into the drug structure can minimize the chances of CYP450-based drug-drug interactions. In other words, an alternate, non-CYP450, metabolic pathway acts as a built-in escape route when a multi-drug therapeutic regimen causes CYP450 interactions to occur. For example, fenoldopam, an antihypertensive agent, is metabolized via 3 parallel and independent metabolic routes that are not based on CYP450: methylation via catechol O-methyl transferase, glucuronidation, and sulfation. Similarly, raloxifene undergoes extensive first pass metabolism by the liver and the major metabolites are the 6-glucuronide, the 4'-glucuronide, and the 6,4'-diglucuronide conjugates, which are not dependent on CYP450. Consequently, no significant metabolic drug interactions with inhibitors of CYP450 are known for fenoldopam and raloxifene.

Remifentanil, an ultra-short opioid used as analgesic during induction and maintenance of general anesthesia, further illustrates this point. Remifentanyl is metabolized extensively by esterases, which are non-oxidative, not CYP450-dependent, enzymes. Following i.v. administration, remifentanil is rapidly metabolized in the blood and other tissues. As a consequence, the elimination of remifentanil is independent of renal and hepatic function [Dershwitz, M., et al. (1996) Anesthesiology 84:812–820], and no clinically significant metabolic drug-drug interactions have been reported.

Elevation of LFT can be idiosynchratic, i.e., its true source is unknown but is probably linked to a genetic variation in the patient population. However, the vast majority of LFT elevations are not idiosynchratic. Regardless, LFT elevations are a direct indicator of hepatocyte toxicity and are due to the accumulation of a toxic compound in hepatocytes. The term accumulation is used herein to indicate that the concentrations of toxic compound in the hepatocyte is larger than that which can be safely eliminated by the cell. The toxic compound can be either the drug itself or the metabolite(s).

In some cases, LFT elevations can be traced to the formation of a reactive metabolic intermediate. The body has natural detoxification systems to eliminate reactive intermediates. When the detoxification systems fail, reactive intermediates are free to react with endogenous molecules, proteins, and even DNA, thus leading to carcinogenicity, theratogenicity, mutations, etc. A well-known example is the carcinogenicity of benzene due to the formation of a reactive epoxide intermediate. This epoxide is normally detoxified by glutathione and/or an epoxide hydrolase. When amounts of benzene are too high however, epoxide hydrolase and glutathione are saturated, and the epoxide becomes toxic, producing rapid LFT elevations and longer-term carcinogenicity.

In other cases, it is the accumulation of the drug itself or one of its metabolites, into the hepatocytes that are the cause of LFT elevations. An example of this is troglitazone (Rezuling). In primary human hepatocyte culture there is a strong positive correlation between hepatocyte toxicity and lack of metabolism of troglitazone, resulting in accumulation and cell death [Kostrubsky, V. E., et al. (2000) Drug Metab. Dips. 28:1192–1197].

Torsade de pointes is a potentially life-threatening cardiac arrhythmia associated with blockade of the rapidly activating component of delayed rectifier potassium channels (IKr) in the myocardium. This channel is expressed from the human homologue of the ether-a-go-go related gene and as such is often referred to by its acronym as the HERG channel [Vandenberg, J. I., et al. (2001) TIPS 22:240–246.]. The arrhythmia resulting from blockade of this receptor is characterized by a dose-dependent prolongation of the QT interval of the surface electrocardiogram. The novel compounds and methods provided by this invention eliminate, or significantly reduce, this undesired activity by optimizing the pharmacology and pharmacodynamics of the metabolite as well as the pharmacokinetics of the drug itself.

QT prolongation resulting in fatal TDP can also be traced to metabolic sources. QT prolongation and TDP happen in the presence of compounds that block the ventricular $IK_R$ channel (Herg channel), therefore delaying repolarization of the ventricle and leading to unresponsiveness of the ventricular muscle to further stimulus and depolarization. The blocking activity on the Herg channel is usually concentration-dependent. Thus, a weak Herg-channel blocker that does not reach inhibitory concentrations at normal therapeutic doses is considered safe. However, when circumstances cause blood levels to rise above normal therapeutic levels and reach levels where $IK_R$ inhibition is substantial, then a small fraction of the population who are genetically predisposed become suddenly at high risk of developing TDP.

This phenomenon of drug accumulation over time can be caused by several factors. In the simplest case it can be an accidental overdose. In other instances, it can be caused by non-linear pharmacokinetics of the drug. The most common reason however is when blood levels suddenly rise due to DDI. This DDI can be at 2 different levels: competition for a carrier-protein binding site, or competition for a metabolizing enzyme. Overdose and DDI were the primary causes for the toxicity of cisapride, a drug that was banned by the FDA in the spring of 2000 for causing unpredictable TDP in patients. In addition, the drugs of this invention are primarily metabolized by non-oxidative pathways that yield water soluble, polar metabolites. Thus, the primary metabolites have reduced, or are devoid of, affinity for the HERG channel. This feature is exemplified in the discovery of fexofenadine which is a carboxylic acid metabolite of the non-sedating antihistamine terfenadine. Both compounds are active as antihistamines but the relatively lipophilic terfenadine is arrhythmogenic at high plasma levels whereas its metabolite is devoid of such activity [Selnick, H. G., et al. (1997) J. Med. Chem. 40:3865–3868].

The pharmacokinetic profile of a compound is governed by its physicochemical properties. The polarity of a molecule affects its volume of distribution such that polar compounds have a comparatively low volume of distribution. This keeps compounds out of the more lipophilic tissues such as the heart and increases the concentration available in plasma. A comparison between terfenadine and astemizole shows a positive correlation between the volume of distribution and the degree of cardiotoxicity [DePonti, F., et al. (2000) QT-interval prolongation by non-cardiac drugs: lessons to be learned from recent experience. Eur. J. Clin. Pharmacol. 56:1–18]. A significant proportion of drug-induced episodes of TDP are the result of an unexpected shift in the metabolic pathway due to a drug-drug-interaction, genetic trait, or overdose. The cause is the same in each case: the primary metabolic pathway is blocked and drug accumulates to a toxic level.

Mibefradil is a calcium channel blocker with a unique mechanism of action in that it not only blocks L- but also T-type channels. Clinically, this agent is distinguished from other calcium channel blockers by its minimal effect on heart rate and a lack of reducing cardiac contractility. While mibefradil demonstrated efficacy in the treatment of hypertension and angina pectoris in man, the drug was eventually withdrawn by the manufacturer due to drug-drug interactions based on inhibition of cytochrome P-450, in particular the CYP3A4-isozyme which is the main metabolizing liver enzyme for mibefradil and a large number of other drugs. Therefore, it would be very desirable to provide compounds with the therapeutic advantages of mibefradil but which would not have the aforementioned disadvantages.

The development of new chemical entities (NCE) that do not induce or inhibit CYP450 and whose metabolism is not altered by other drugs is highly desirable and are sought by pharmaceutical companies. The subject invention provides novel compounds and compositions having a metabolic pathway that is well characterized, primarily non-oxidative, and difficult to overwhelm.

BRIEF SUMMARY OF THE INVENTION

The subject invention provides useful and novel calcium channel blockers. The subject invention also provides methods for synthesizing the compounds of the invention. The invention also provides methods for the control or prevention of hypertension, angina pectoris, ischemia, arrhythmias, and cardiac insufficiency in a patient by administering a compound, or composition, of the invention to an individual in need of such treatment.

Advantageously, the subject invention provides compounds which are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of calcium channel blocking treatment This invention is drawn to compounds which are more easily metabolized by the metabolic drug detoxification systems. This invention is also drawn to methods of treating disorders which can be treated by blocking calcium channels. Specifically, this invention provides analogs of drugs which have been designed to be more susceptible to degradation by hydrolases, particularly serum and/or cytosolic esterases and methods of treatment comprising the administration of these analogs to individuals.

DETAILED DISCLOSURE OF THE INVENTION

The subject invention concerns novel calcium channel blockers. Preferably, the calcium channel blocker can be deactivated to a primary inactive metabolite by hydrolytic enzymes. Compounds of the present invention can be advantageously used to treat individuals suffering from cardiovascular diseases as exemplified by hypertension, angina pectoris, ischemia, arrhythmias and congestive heart failure. Many of these individuals are taking multiple drugs, thus, the compounds of the subject invention would be much safer in view of the reduced or eliminated incidence of DDI, LFT, and/or TDP.

Figure 1:
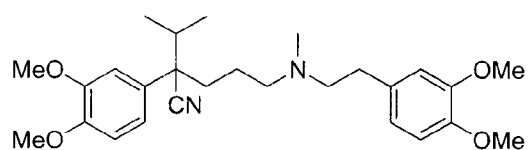
FIG. 1 depicts various structural classes of calcium blockers currently marketed in the United States.
Figure 1:
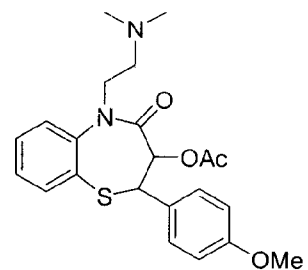
Figure 1:
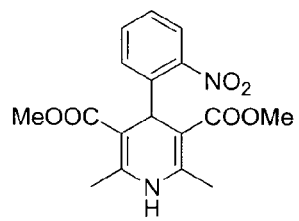
Figure 1:
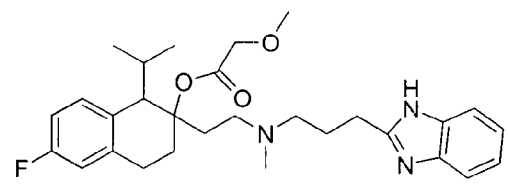
Figure 2:
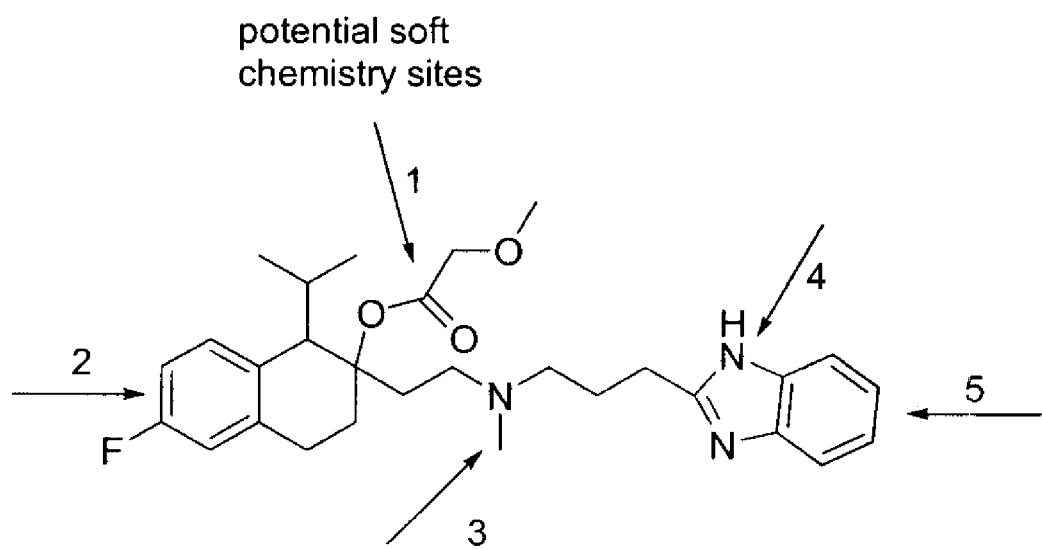
FIG. 2 provides exemplary illustrations of points at which mibefradil can be modified to provide compounds of the invention.
Figure 3:
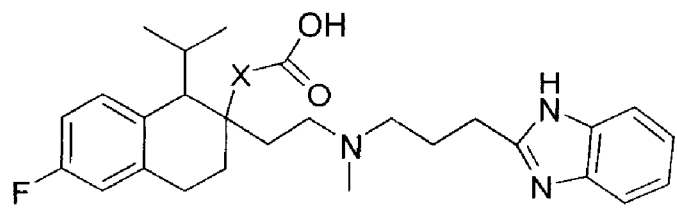
FIGS. 3–9 illustrate the formation of primary inactive metabolites arising from the metabolism of compounds of the invention by the action of hydrolytic enzymes.
Figure 3:
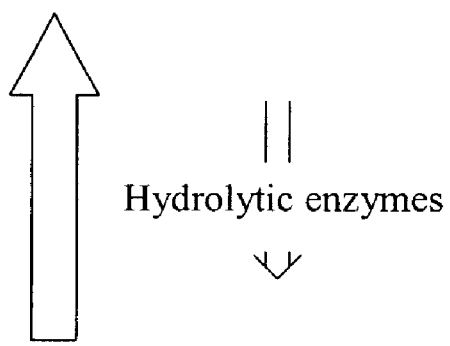
Figure 3:
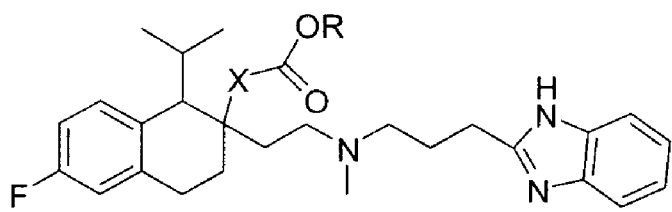
Figure 4:
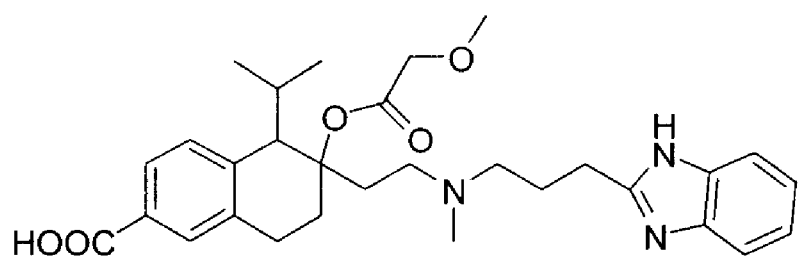
Figure 4:
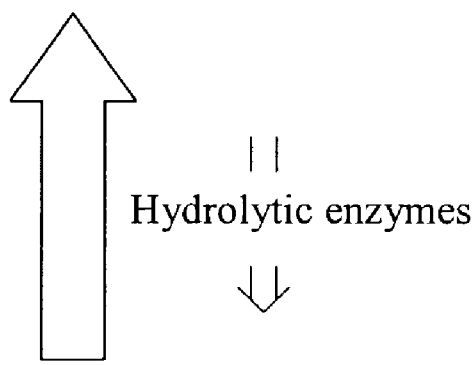
Figure 4:
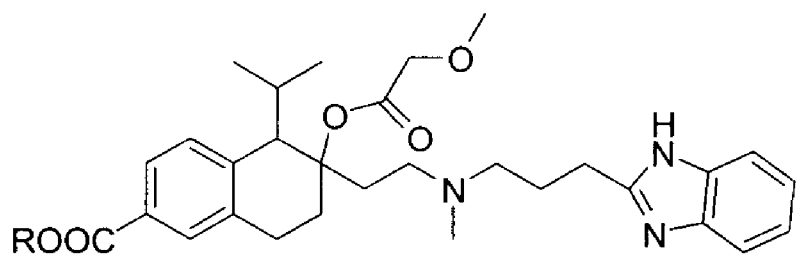
Figure 5:
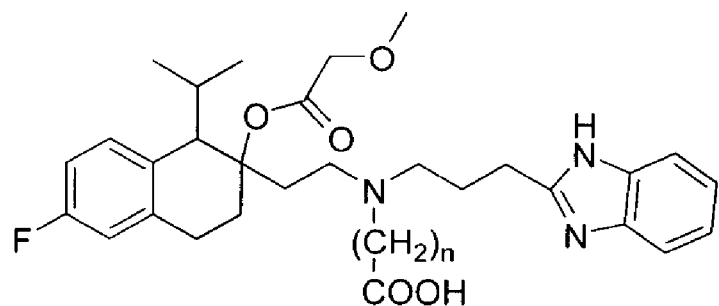
Figure 5:
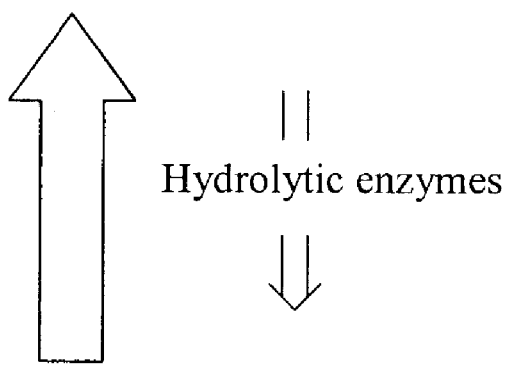
Figure 5:
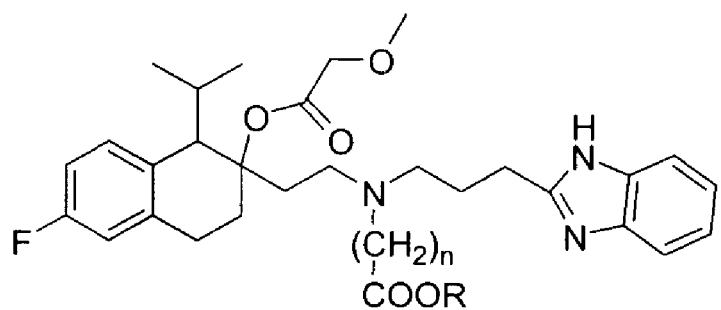
Figure 6:
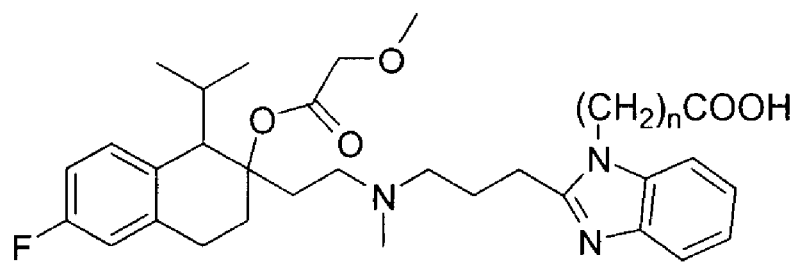
Figure 6:
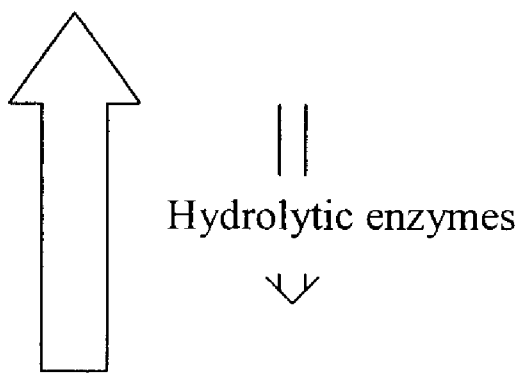
Figure 6:
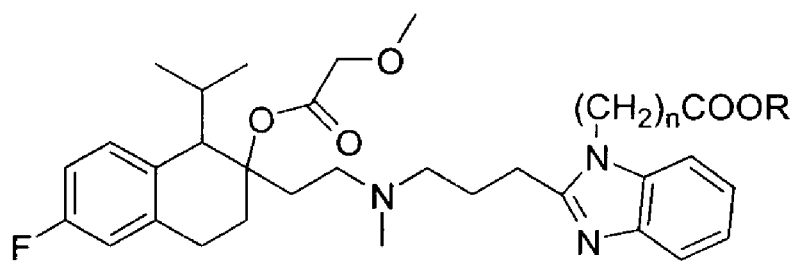
Figure 7:
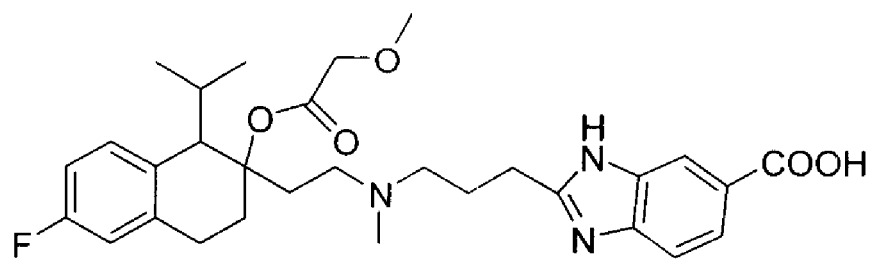
Figure 7:
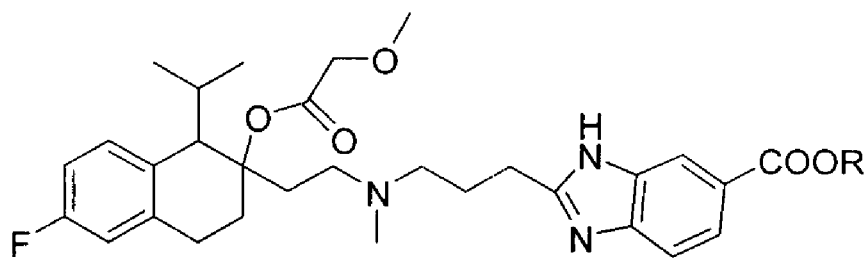
Figure 8:
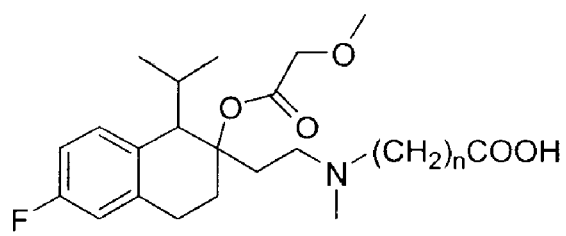
Figure 8:
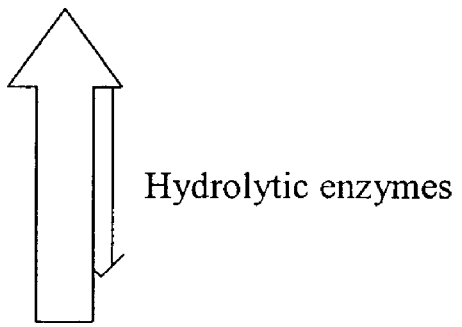
Figure 8:
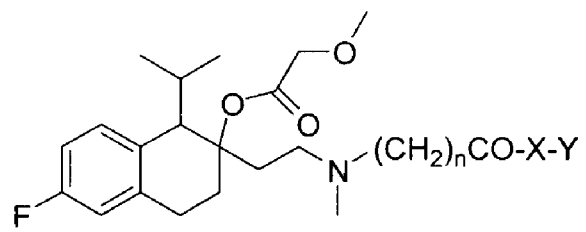
Figure 9:
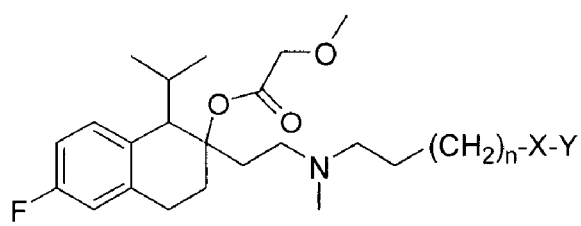
Figure 9:
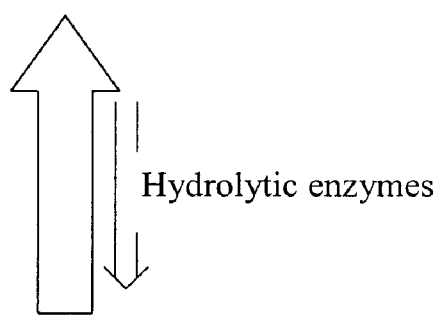
Figure 9:
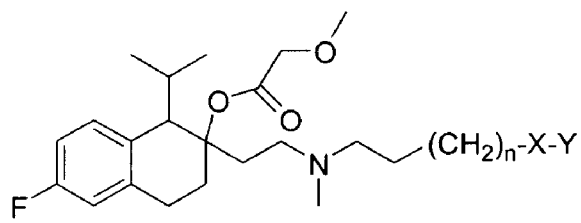

Verapamil, diltiazem, and nifedipine represent three different structural classes of calcium entry blockers and are all currently marketed in the United States (FIG. 1). However, these compounds do not demonstrate the same kind of clinical benefit as mibefradil since they tend to decrease myocardial contractive force. Accordingly, in a preferred embodiment, the present invention provides novel mibefradil-based compounds that have been modified to provide for metabolism via endogenous hydrolytic enzymes (FIG. 2). The novel compounds are referred to as soft calcium channel blockers, i.e. bioactive molecules having cardiovascular properties and undergoing deactivation to primary inactive metabolites by hydrolytic enzymes. FIGS. 3–9 provide exemplary metabolic degradation routes for exemplary compounds of the invention.

Additional modifications of the compounds disclosed herein can readily be made by those skilled in the art. Thus, analogs and salts of the exemplified compounds are within the scope of the subject invention. With a knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

In a preferred embodiment, the subject invention provides compounds having the following formula:

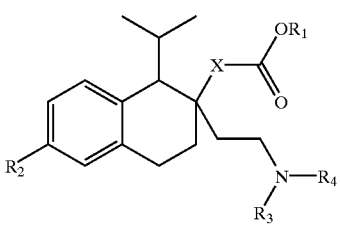

wherein:
X=a bond, $(CH_2)_n$, O, S, or $O(CH_2)_n$,
  wherein n=1–6;
$R_1$=$C_{1-6}$ alkyl, optionally substituted with OH or $NH_2$;
$R_2$=F or $COOR_5$,
  wherein $R_5$ is $C_{1-6}$ alkyl, optionally substituted with OH or $NH_2$;
$R_3$=$CH_3$ or $(CH_2)_n$—$COOR_6$,
  wherein n=1–6 and $R_6$ is $C_{1-6}$ alkyl, optionally substituted with OH or $NH_2$;
$R_4$=$(CH_2)_n$—$COR_7R_8$, —$(CH_2)_n$—$R_{10}R_{11}$ or

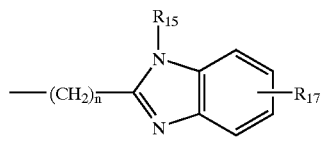

$R_7$=O, NH, or $NR_9$,
$R_8$=optionally substituted aryl or heterocycle,
$R_9$=$C_{1-6}$ alkyl,
$R_{10}$=O, S, SO, $SO_2$, NH, $NR_{12}$ or $N(CH_2)_m$ $COOR_{13}$,
$R_{11}$=aryl or heterocyclyl optionally substituted with $(CH_2)_n$ $COOR_{14}$,
$R_{12}$=$C_{1-6}$ alkyl, optionally substituted with OH or $NH_2$,
$R_{13}$=$C_{1-6}$ alkyl, optionally substituted with OH or $NH_2$,
$R_{14}$=$C_{1-6}$ alkyl, optionally substituted with OH or $NH_2$,
$R_{15}$=$(CH_2)_n$ $COOR_{16}$,
$R_{16}$=$C_{1-6}$ alkyl, optionally substituted with OH or $NH_2$,
$R_{17}$=not present or $COOR_{18}$ wherein $R_{18}$ is $C_{1-6}$ alkyl, optionally substituted with OH or $NH_2$, and
wherein n=1–6.

The subject invention further pertains to enantiomerically isolated compounds, and compositions comprising the compounds, for calcium channel blocking. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

A further aspect of the subject invention pertains to the breakdown products which are produced when the therapeutic compounds of the subject invention are acted upon by hydrolytic enzymes, such as esterases. The presence of these breakdown products in urine or serum can be used to monitor the rate of clearance of the therapeutic compound from a patient.

Thus, the subject invention also provides antibodies that specifically react with metabolic breakdown products of the subject invention as wells as detection assays for the identification of metabolic breakdown products in the serum or urine of an individual. In some preferred embodiments, the antibodies specific for the metabolic breakdown products of the invention do not cross-react with the therapeutic compounds (i.e., soft calcium channel blockers) of the invention. Other embodiments provide for antibodies that do not specifically bind to metabolic breakdown products of the soft calcium channel blockers but which specifically bind to non-metabolized (intact) soft calcium channel blockers of the subject invention. In yet other embodiments, antibodies that specifically bind to both metabolic breakdown products and intact compounds of the invention are provided. The subject invention also provides for kits containing any combination of the antibodies discussed supra and/or containing soft calcium blockers of the invention and/or metabolic breakdown products of the invention. In some embodiments, the kits of the invention include assay substrates (e.g., immunoassay plates or substrates upon which lateral flow assays are performed) coated with antibodies or biosensors containing antibodies of the invention. Alternatively, assay substrates or biosensors can be coated with intact compounds or metabolic breakdown products of the inventive compounds. Other embodiments provide various combinations of antibodies, intact compounds, and metabolic breakdown products coated on assay substrates or biosensors.

The term "antibody" encompasses polyclonal and monoclonal antibody preparations, as well as preparations including hybrid antibodies, genetically altered antibodies (including antibodies modified to alter their physiochemical characteristics and antibodies subjected to affinity mutagenesis to increase or decrease their binding affinities (e.g., through alanine scanning mutagenesis)), $F(ab')_2$ fragments, F(ab) fragments, $F_v$ fragments, single domain antibodies, chimeric antibodies, diabodies, multispecific antibodies, humanized antibodies, and functional fragments thereof which exhibit immunological binding properties of the parent antibody molecule. Methods of making polyclonal, recombinant, and monoclonal antibodies, as well as antigen binding fragments of such antibodies, are well-known in the art.

Detection systems for the identification of metabolic breakdown products present in the serum or urine of an individual include ligand-receptor binding assays. Non-limiting examples of such assays can include antibody-based assays such as enzyme linked immunosorbent assays (ELISAs), radioimmunoassays (RIAs), lateral flow assays, automated flow assays, and assays utilizing antibody containing biosensors. The assays and methods for conducting the assays are well-known in the art. Ligand-receptor binding assays can be considered to be of four types: direct binding, sandwich assays, competition assays, and displacement assays. While the exact arrangement of ligands and receptors varies widely as does the type of readout system involved, the four types can be generally (but not exclusively) described as follows.

In a direct binding assay, either the ligand or receptor is labeled, and there is a means of measuring the number of complexes formed. In a sandwich assay, the formation of a complex of at least three components (e.g., receptor-ligand-labeled receptor) is measured. In a competition assay, labeled ligand and unlabelled ligand compete for binding to the receptor, and either the bound or the free component is measured. In a displacement assay, the labeled ligand is prebound to the receptor, and a change in signal is measured as the unlabelled ligand displaces the bound labeled ligand from the receptor.

Displacement assays and flow immunosensors useful for carrying out displacement assays are described in: (1) Kusterbeck et al., "Antibody-Based Biosensor for Continuous Monitoring," in *Biosensor Technology*, R. P. Buck et al., eds., Marcel Dekker, N.Y. pp. 345–350 (1990); Kusterbeck et al., "A Continuous Flow Immunoassay for Rapid and Sensitive Detection of Small Molecules," *Journal of Immunological Methods*, vol. 135, pp. 191–197 (1990); Ligler et al., "Drug Detection Using the Flow Immunosensor," in Biosensor Design and Application, J. Findley et al, eds., American Chemical Society Press, pp. 73–80 (1992); and Ogert et al., "Detection of Cocaine Using the Flow Immunosensor," *Analytical Letters*, vol. 25, pp. 1999–2019 (1992), all of which are incorporated herein by reference in their entireties. Displacement assays and flow immunosensors are also described in U.S. Pat. No. 5,183,740, which is also incorporated herein by reference in its entirety. The displacement immunoassay, unlike most of the competitive immunoassays used to detect small molecules, can generate a positive signal with increasing antigen concentration.

Figure 10:
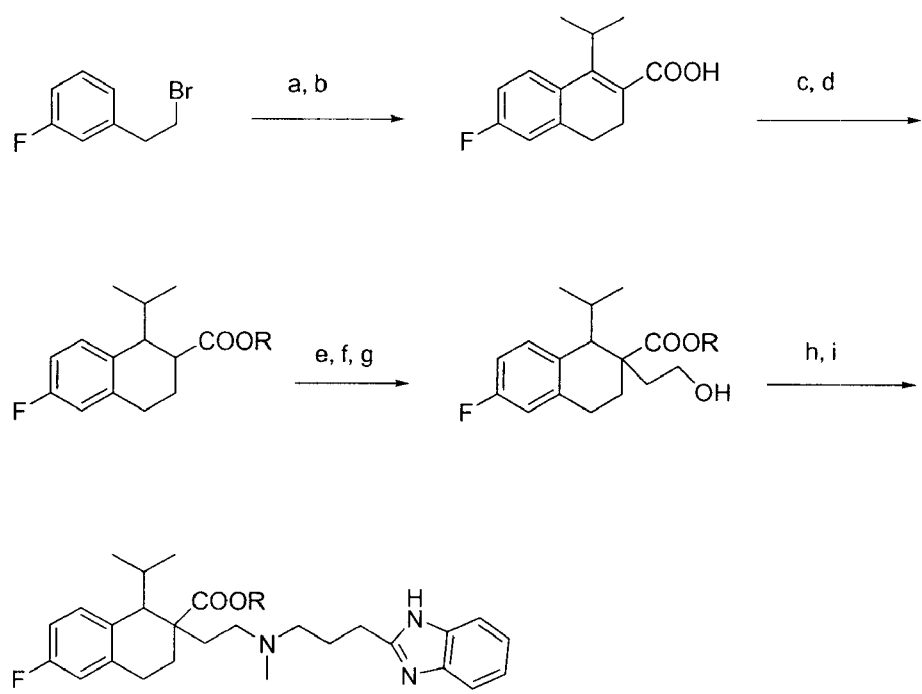
FIGS. 10–12 are exemplary synthetic schemes for producing compounds of the invention.
Figure 11:
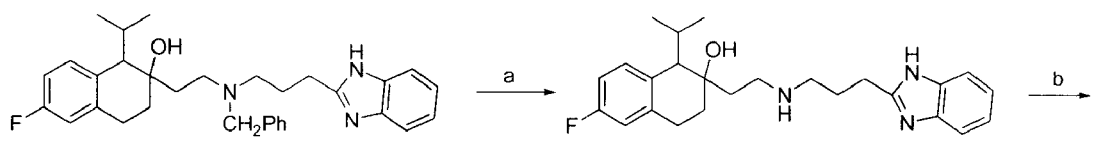
Figure 11:
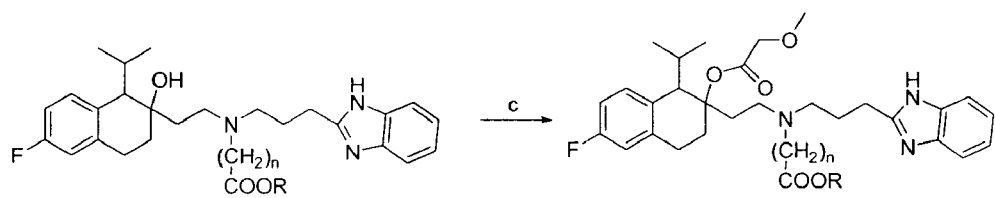
Figure 11:
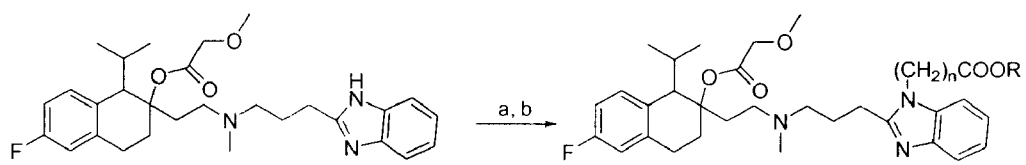
Figure 12:
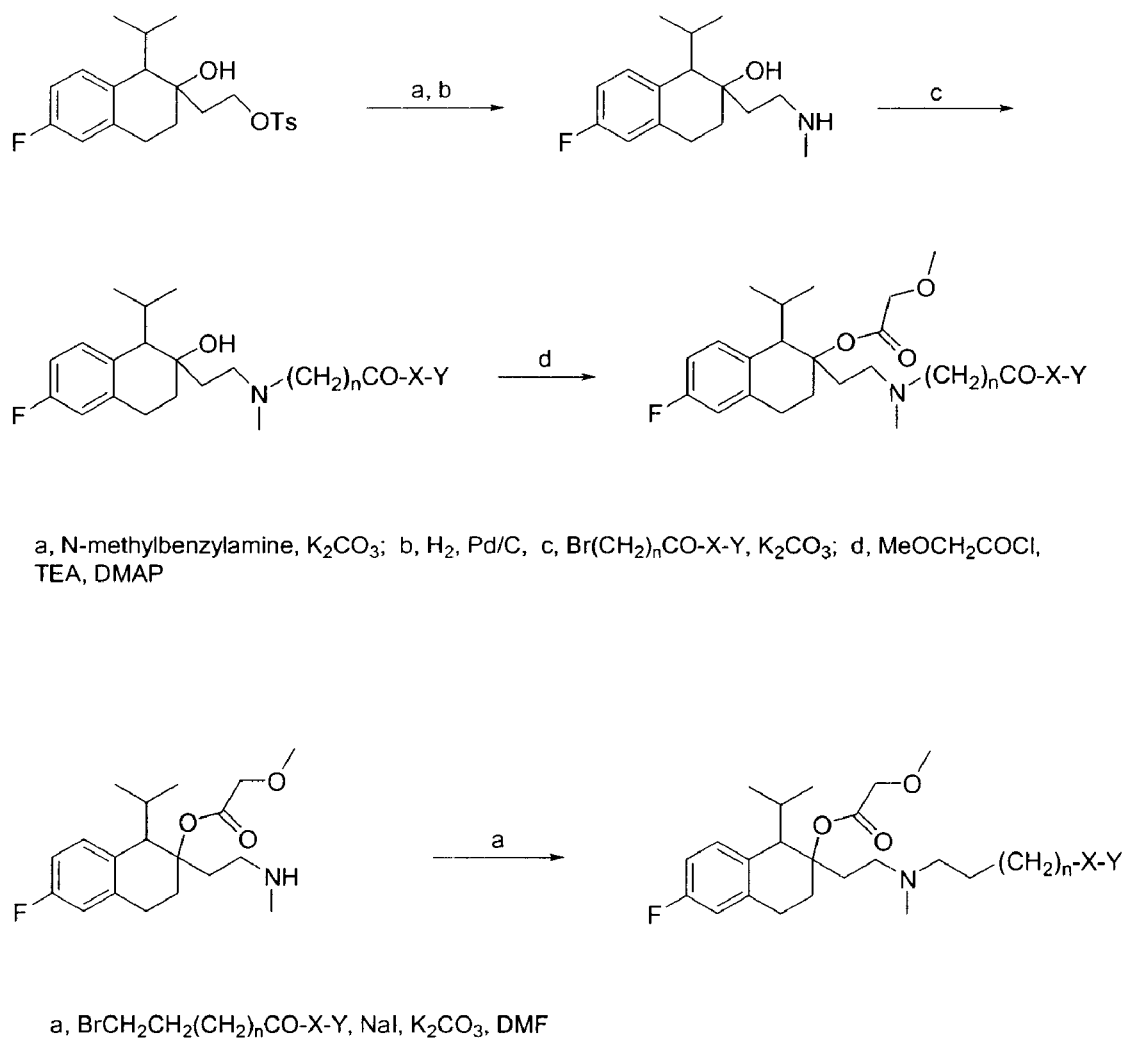

The subject invention further provides methods of synthesizing the unique and advantageous therapeutic compounds of the subject invention. Particularly, methods of producing less toxic therapeutic agents comprising introducing ester groups into therapeutic agents are taught. The ester linkage may be introduced into the compound at a site which is convenient in the manufacturing process for the compounds of the invention. Various exemplary synthetic routes for the preparation of the compounds of the subject invention are described in FIGS. 10–12. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

The term "individual(s)" is defined as a single mammal to which is administered a compound or composition of the present invention. The mammal may be, for example a mouse, rat, pig, horse, rabbit, goat, pig, cow, cat, dog, or human. In a preferred embodiment, the individual is a human.

The compounds of this invention have therapeutic properties similar to those of the unmodified parent compounds. Accordingly, dosage rates and routes of administration of the disclosed compounds are similar to those already used in the art and known to the skilled artisan. (See, for example, Physicians' Desk Reference. 54$^{th}$ Ed., Medical Economics Company, Montvale, N.J., 2000.)

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulation which can be used in connection with the subject invention. In general, the compositions of the subject invention are formulated such that an effective amount of the bioactive compound(s) is combined with a suitable carrier in order to facilitate effective administration of the composition.

In accordance with the subject invention, pharmaceutical compositions are provided which comprise, as an active ingredient, an effective amount of one or more of the compounds and one or more non-toxic, pharmaceutically acceptable carriers or diluents. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances that may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid: based preparation or formulated to be incorporated into solid food products, chewing gum, or lozenges.

All patents, patent applications, provisional applications, and publications referred to or cited herein are incorporated by reference in their entirety, including all figures and tables, to the extent they are not inconsistent with the explicit teachings of this specification.

It should understood that the examples and embodiments described herein are for illustrative purpose only and that varios modifications or changes in light thereof will be suggested to persons skilled in the art and are to be included within the spirit and purview of this application.

We claim:

1. A calcium channel blocker compound having the following structure:

$R_4=$

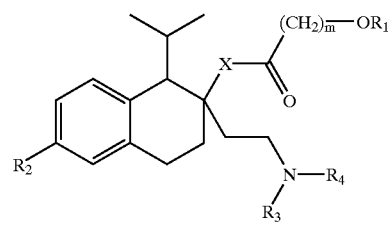

wherein:

$X=$ a bond, $(CH_2)_n$, O, S, or $O(CH_2)_n$, $R=C_{1-6}$ alkyl, optionally substituted with OH or $NH_2$;

$R_2=F$ or $COOR_5$,
  wherein $R_5$ is $C_{1-6}$ alkyl, optionally substituted with OH or $NH_2$;

$R_3=CH_3$ or $(CH_2)_n$—$COOR_6$,
  wherein $R_6$ is $C_{1-6}$ alkyl, optionally substituted with OH or $NH_2$;

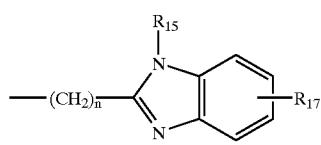

$R_7$=O, NH, or $NR_9$, $R_8$=optionally substituted aryl or heterocycle, $R_9$=$C_{1-6}$ alkyl, $R_{10}$=O, S, SO, $SO_2$, NH, $NR_{12}$ or $N(CH_2)_m\ COOR_{13}$, $R_{11}$=aryl or heterocyclyl optionally substituted with $(CH_2)_n\ COOR_{14}$, $R_{12}$=$C_{1-6}$ alkyl, optionally substituted with OH or $NH_2$, $R_{13}$=$C_{1-6}$ alkyl, optionally substituted with OH or $NH_2$, $R_{14}$=$C_{1-6}$ alkyl, optionally substituted with OH or $NH_2$, $R_{15}$=$(CH_2)_n\ COOR_{16}$, $R_{16}$=$C_{1-6}$ alkyl, optionally substituted with OH or $NH_2$, $R_{17}$=not present or $COOR_{18}$ wherein $R_{18}$ is $C_{1-6}$ alkyl, optionally substituted with OH or $NH_2$, and wherein n=1–6 and m=0 or 1.

2. A calcium channel blocker compound having a formula selected from the group consisting of:

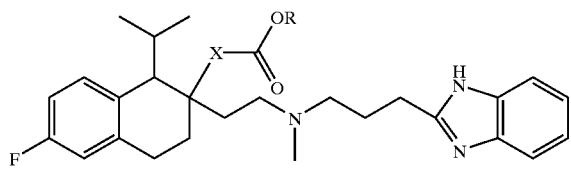

X=bond, $CH_2$, or $OCH_2$

R=lower alkyl optionally substituted with OH or $NH_2$;

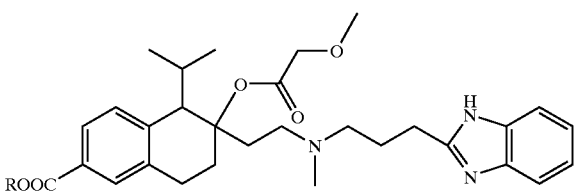

R=lower alkyl optionally substituted with OH or $NH_2$;

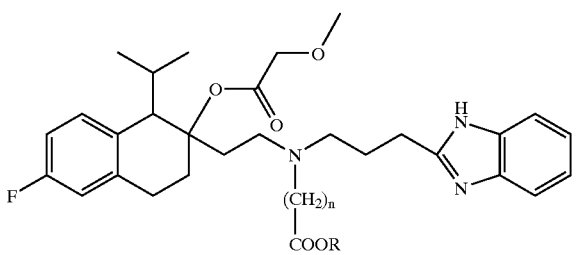

n=1 to 3

R=lower alkyl optionally substituted with OH or $NH_2$;

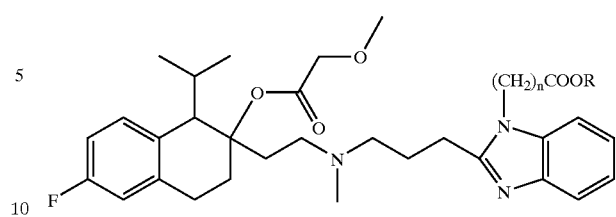

n=1 to 3

R=lower alkyl optionally substituted with OH or $NH_2$;

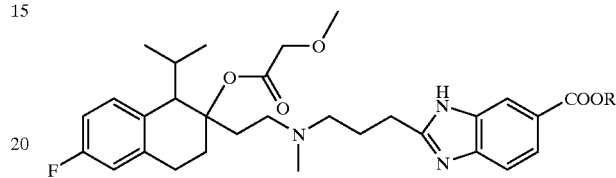

R=lower alkyl optionally substituted with OH or $NH_2$.

3. The compound, according to claim 2, having the following structure:

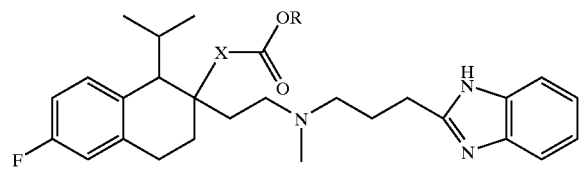

X=bond, $CH_2$ or $OCH_2$

R=lower alkyl optionally substituted with OH or $NH_2$.

4. The compound, according to claim 2, having the following structure:

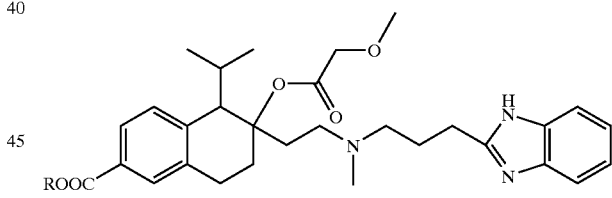

R=lower alkyl optionally substituted with OH or $NH_2$.

5. The compound, according to claim 2, having the following structure:

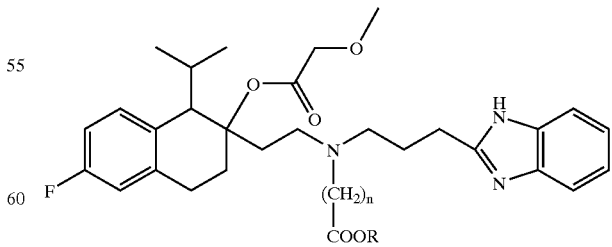

n=1 to 3

R=lower alkyl optionally substituted with OH or $NH_2$.

6. The compound, according to claim 2, having the following structure:

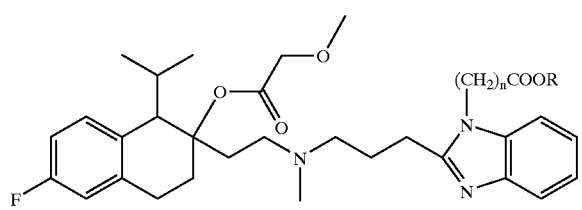

n=1 to 3

R=lower alkyl optionally substituted with OH or $NH_2$.

7. The compound, according to claim 2, having the following structure:

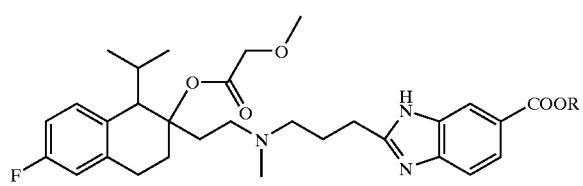

R=lower alkyl optionally substituted with OH or $NH_2$.

8. A pharmaceutical composition comprising a calcium channel blocker compound having the following structure:

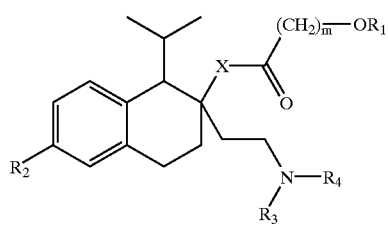

wherein:

X=a bond, $(CH_2)_n$, O, S, or $O(CH_2)_n$, $R_1$=$C_{1-6}$ alkyl, optionally substituted with OH or $NH_2$;

$R_2$=F or $COOR_5$,
 wherein $R_5$ is $C_{1-6}$ alkyl, optionally substituted with OH or $NH_2$;

$R_3$=$CH_3$ or $(CH_2)_n$—$COOR_6$,
 wherein $R_6$ is $C_{1-6}$ alkyl, optionally substituted with OH or $NH_2$;

$R_4$=

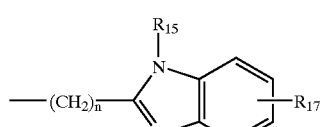

$R_7$=O, NH, or $NR_9$, $R_8$=optionally substituted aryl or heterocycle, $R_9$=$C_{1-6}$ alkyl, $R_{10}$=O, S, SO, $SO_2$, NH, $NR_{12}$ or $N(CH_2)_m$ $COOR_{13}$, $R_{11}$=aryl or heterocyclyl optionally substituted with $(CH_2)_n$ $COOR_{14}$, $R_{12}$=$C_{1-6}$ alkyl, optionally substituted with OH or $NH_2$, $R_{13}$=$C_{1-6}$ alkyl, optionally substituted with OH or $NH_2$, $R_{14}$=$C_{1-6}$ alkyl, optionally substituted with OH or $NE_2$, $R_{15}$=$(CH_2)_n$ $COOR_{16}$, $R_{16}$=$C_{1-6}$ alkyl, optionally substituted with OH or $NH_2$, $R_{17}$=not present or $COOR_{18}$ wherein $R_{18}$ is $C_{1-6}$ alkyl, optionally substituted with OH or $NH_2$, and wherein n=1–6 and m=O or 1.

9. A pharmaceutical composition comprising a calcium channel blocker compound having a formula selected from the group consisting of:

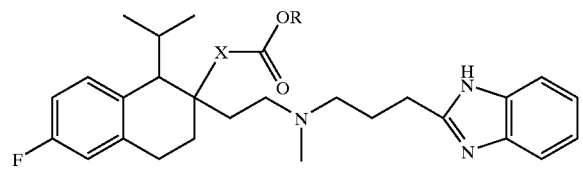

X=bond, $CH_2$, or $OCH_2$

R=lower alkyl optionally substituted with OH or $NH_2$;

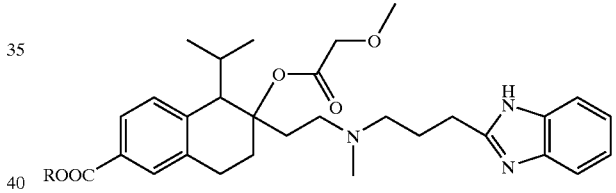

R=lower alkyl optionally substituted with OH or $NH_2$;

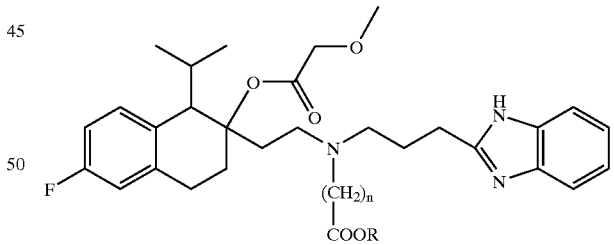

n=1 to 3

R=lower alkyl optionally substituted with OH or $NH_2$;

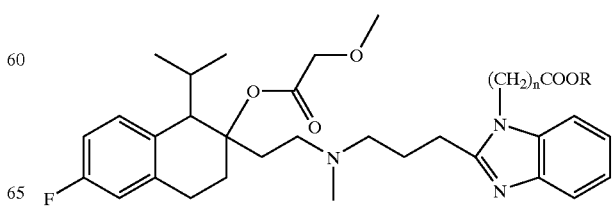

n=1 to 3

R=lower alkyl optionally substituted with OH or NH$_2$;

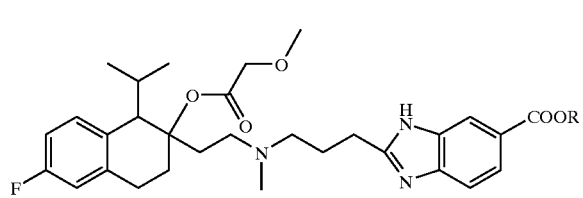

R=lower alkyl optionally substituted with OH or NH$_2$.

10. The composition, according to claim 9, comprising a compound having the following structure:

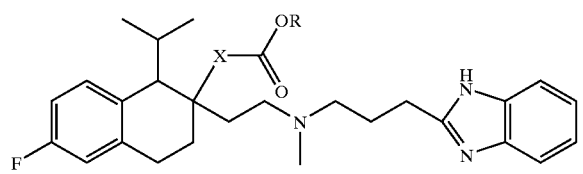

X=bond, CH$_2$, or OCH$_2$

R=lower alkyl optionally substituted with OH or NH$_2$.

11. The composition, according to claim 9, having the following structure:

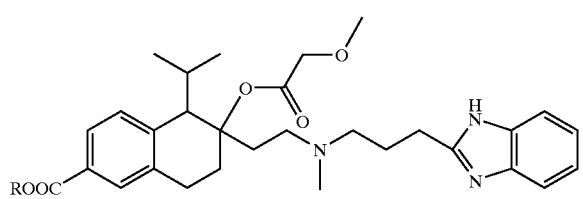

R=lower alkyl optionally substituted with OH or NH$_2$.

12. The composition, according to claim 9, having the following structure:

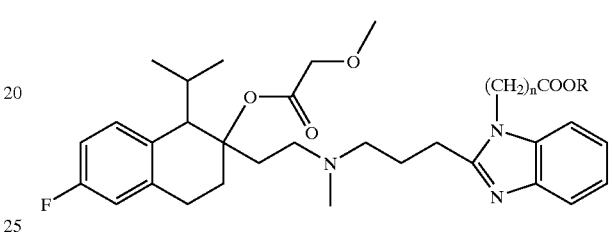

n=1 to 3

R=lower alkyl optionally substituted with OH or NH$_2$.

13. The composition, according to claim 9, having the following structure:

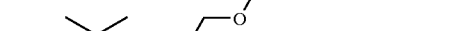

n=1 to 3

R=lower alkyl optionally substituted with OH or NH$_2$.

14. The composition, according to claim 9, having the following structure:

R=lower alkyl optionally substituted with OH or NH$_2$.

* * * * *

UNITED STATES PATENT AND TRADEMARK OFFICE
CERTIFICATE OF CORRECTION

PATENT NO.    : 6,608,097 B2                                        Page 1 of 2
DATED         : August 19, 2003
INVENTOR(S)   : Pascal Druzgala et al.

It is certified that error appears in the above-identified patent and that said Letters Patent is hereby corrected as shown below:

Column 3,
Line 65, "(Rezuling)" should read -- (Rezulin®) --.

Column 14,
Line 11, "$NE_2$" should read -- $NH_2$ --.

Column 10, lines 42-66 and Column 11 lines 1-5,
"A calcium channel blocker compound having the following structure:

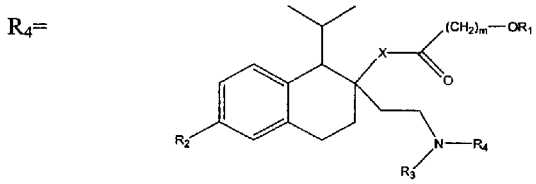

wherein:
    X=a bond, $(CH_2)_n$, O, S, or $O(CH_2)_n$,
    R=$C_{1-6}$ alkyl, optionally substituted with OH or $NH_2$;
    $R_2$=F or $COOR_5$,
        wherein $R_5$ is $C_{1-6}$ alkyl, optionally substituted with OH or $NH_2$;
    $R_3$=$CH_3$ of $(CH_2)_n$ - $COOR_6$,
        wherein $R_6$ is $C_{1-6}$ alkyl, optionally substituted with OH or $NH_2$;

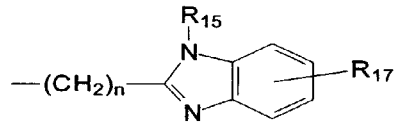

$R_7$=O, NH, or $NR_9$,"

should read
       -- A calcium channel blocker compound having the following structure:

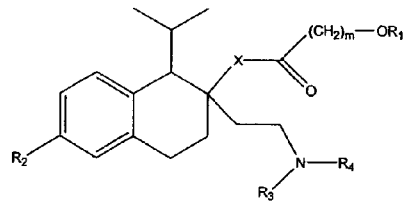

UNITED STATES PATENT AND TRADEMARK OFFICE
CERTIFICATE OF CORRECTION

PATENT NO. : 6,608,097 B2
DATED : August 19, 2003
INVENTOR(S) : Pascal Druzgala et al.

It is certified that error appears in the above-identified patent and that said Letters Patent is hereby corrected as shown below:

<u>Column 10, lines 42-66 and Column 11 lines 1-5 cont'd,</u>
wherein:
   X=a bond, $(CH_2)_n$, O, S, or $O(CH_2)_n$,
   R=$C_{1-6}$ alkyl, optionally substituted with OH or $NH_2$;
   $R_2$=F or $COOR_5$,
     wherein $R_5$ is $C_{1-6}$ alkyl, optionally substituted with OH or $NH_2$;
   $R_3$=$CH_3$ or $(CH_2)_n$ - $COOR_6$,
     wherein $R_6$ is $C_{1-6}$ alkyl, optionally substituted with OH or $NH_2$;

$R_4$=

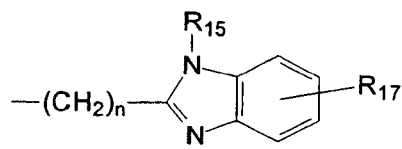

$R_7$=O, NH, or $NR_9$,".

Signed and Sealed this

Third Day of February, 2004

JON W. DUDAS
*Acting Director of the United States Patent and Trademark Office*